US006953799B1

(12) United States Patent  (10) Patent No.: US 6,953,799 B1
Henry et al.  (45) Date of Patent: Oct. 11, 2005

(54) MODULATION OF CELL FATES AND ACTIVITIES BY DIKETO PHTHALAZINES

(75) Inventors: Mark O. Henry, North Andover, MA (US); William S. Lynn, Hillsborough, NC (US)

(73) Assignee: Bach Pharma, Inc., North Andover, MA (US)

( * ) Notice: Subject to any disclaimer, the term of this patent is extended or adjusted under 35 U.S.C. 154(b) by 73 days.

(21) Appl. No.: 10/283,647

(22) Filed: Oct. 30, 2002

(51) Int. Cl.$^7$ ......................................... A61K 31/495
(52) U.S. Cl. ..................................................... 514/248
(58) Field of Search ......................... 514/18, 152, 171, 514/248, 250, 440, 562

(56) References Cited

U.S. PATENT DOCUMENTS

| 5,512,573 | A | * | 4/1996 | Minin et al. | ................. | 514/248 |
| 5,543,410 | A | * | 8/1996 | Minin et al. | ................. | 514/248 |
| 5,633,282 | A | * | 5/1997 | Collins et al. | ............... | 514/622 |
| 5,719,151 | A | * | 2/1998 | Shall et al. | ................. | 514/248 |
| 5,874,444 | A | * | 2/1999 | West | ........................... | 514/310 |

OTHER PUBLICATIONS

Teh Merck Index, 11$^{th}$ ed. Published by Merck & Co., Inc. (NJ), 1989, pp 463-464, cit.#2922.*
Cecil Textbook of Medicine, 21$^{st}$ ed., vol. 1, Goldman et al. (eds.), published 2000 by W.B. Saunders Company, pp1060-74.*
Stedman's Medical Dictionary, 25$^{th}$ edition, published 1990 by Williams & Wilkins, pp. 435 and 1393.*
Ali Abdel-Rahman et al., Disruption of the Blood-Brain Barrier and Neuronal Cell Death in Cingulate Cortex. Dentate Gyrus, Thalamus, and . . . Neurobiology of Disease 10, May 24, 2002, pp. 306-326.
L. Alvarez et al., Dorsal Subthalamotomy for Parkinson's Disease, Movement Disorders, 2001, pp. 72-78, vol. 16, No. 1.
R. A. Armstong et al., The Levels of Neopterin, Biopterin and the Neopterin/Biopterin Ratio in Urine from Control Subjects and Patients with Alzheimer's Disease and Down's Syndrome, Pteridines, 1995, pp. 185-189. vol. 6. No. 4.
Jeffrey S. Armstrong et al., Glutathione Depletion Enforces the Mitochondrial Permeability Transistion and Causes Cell Death in HL60 Cells that Overexpress Bcl-2, The FASEB Journal, Jun. 7, 2002, 18 pages, express article 10.1096/fj.02-0097fje.
Avinash Bhandoola et al., Immature Thymocytes Undergoing Receptor Rearrangements Are Resistant to an Atm-dependent Death Pathway Activated in Mature T Cells by Double-stranded DNA Breaks. The Journal of Experimental Medicine. Sep. 18, 2000, pp. 891-897. vol. 192. No. 6.
Minghua Chen et al., Minocycline Inhibits Caspase-1 and Caspase-3 Expression and Delays Mortality in a Transgenic Mouse Model of Huntington Disease, Nature Medicine, Jul. 2000, pp. 797-801. vol. 6. No. 7.

Terry P. Combs et al., Induction of Adipocyte Complement-Related Protein of 30 Kilodaltons by PPARy Agonists: A Potential Mechanism of Insulin Sensitization, Endocrinology, 2002, pp. 998-1007.
Paola Costantini et al., Oxidation of a Critical Thiol Residue fo the Adenine Nucleotide Translocator Enforces Bcl-2-independent Permeability Transition Pore Opening and Apoptosis, Oncogene, 2000, pp. 307-314.
Paola Costantini et al., Modulation of the Mitochondrial Permeability Transition Pore by Pyridine Nucleotides and Dithiol Oxidation at Two Separate Sites, The Journal of Biological Chemistry, Mar. 22, 1996, pp. 6746-6751, vol. 271, No. 12.
Christophe Crochemore et al., Enhancement of p53 Activity and Inhibition of Neural Cell Proliferation by Glucocorticoid Receptor Activation, The FASEB Journal, Jun. 2002, pp. 761-770, vol. 16.
Martin Crompton et al., Cyclophilin-D Binds Strongly to Complexes of the Voltage-Dependent Anion Channel and the Adenine Nucleotide Translocase to Form the Permeability Transition Pore, European Journal Biochemistry, 1998, pp. 729-735.
Jan De Boer et al., Premature Aging in Mice Deficient in DNA Repair and Transcription, Science, May 17, 2002, pp. 1276-1279, vol. 296.
Francesca De Giorgi et al., The Permeability Transition Pore Signals Apoptosis by Directing Bax Translocation and Multimerization, The FASEB Journal, Feb. 25, 2002, 20 pages. express article 10.1096/fj.01-0269fje.
Thomas Dehmer et al., Deficiency of Inducible Nitric Oxide Synthase Protects Against MPTP Toxicity in Vivo, Journal of Neurochemistry, 2000, pp. 2213-2216, vol. 74, No. 5.
Yair N. Doza et al., Arsenite Blocks Growth Factor Induced Activation of the MAP Kinase Cascade, Upstream of Ras and Downstream of Grb2-Sos, Onocogene, Jul. 1998, pp. 19-24.
Wulf Droge, Free Radicals in the Physiological Control of Cell Function, Physiological Review, Jan. 2002, pp. 47-95, vol. 82.

(Continued)

Primary Examiner—Raymond J. Henley, III
(74) Attorney, Agent, or Firm—J. Andrea Park

(57) ABSTRACT

Phthalazine diones that function as intracellular redox modulators and buffers are used to treat stressed cells in various disease states in which the intracellular redox status is impaired. By optimal buffering of aberrant redox states, phthalazine diones enhance the cellular processes essential for survival and augment the conventional or other external therapies necessary for treatment. The phthalazine diones of the invention thus regulate cell growth, differentiation, or death to serve as essential adjunctive therapy for the stressed host in various disease states.

6 Claims, No Drawings

OTHER PUBLICATIONS

Yansheng Du et al., Minocycline Prevents Nigrostriatal Dopaminergic Neurodegeneration in the MPTP Model of Parkinson's Disease, Proceedings National Academy Sciences, Dec. 4, 2001, pp. 14669-14674, vol. 98, No. 25.

Anthone W. Dunah et al., Sp I and TAFII130 Transcriptional Activity Disrupted in Early Huntington's Disease, Science, Jun. 21, 2002, pp. 2238-2243, vol. 296.

Gianluigi Forloni et al., Anti-amyloidogenic Activity of Tetracyclines: Studies In Vitro, Federation of European Biochemical Societies, Dec. 15, 2000, pp. 404-407.

Joachim Fruebis et al., Proteolytic Cleavage Product of 30-kDa Adipocyte Complement-related Protein Increases Fatty-Acid Oxidation in Muscle and Causes Weight Loss in Mice, Proceedings National Academy Sciences, Feb. 13, 2001, pp. 2005-2010, vol. 98, No. 4.

Teruo Hayashi et al., Possible Mechanism of Dantrolene Stabilization of Cultured Neuroblastoma Cell Plasma Membranes, Journal of Neurochemistry, 1994, pp. 1849-1854, vol. 63, No. 5.

Lihua He et al., Hypothesis—Regulated and Unregulated Mitochondrial Permeability Transition Pores: A New Paradigm of Pore Structure and Function?, Federation of European Biochemical Societies, Jan. 4, 2002, pp. 1-7.

Kiichi Hirota et al., AP-I Transcriptional Activity is Regulated by a Direct Association Between Thioredoxin and Ref-1, Proceedings National Academy of Sciences, Apr. 1997, pp. 3633-3638, vol. 94.

Feng Hong et al., Cyclosporine Blocks Muscle Differentiation by Inducing Oxidative Stress and By Inhibiting the Peptidylprolyl-cis-trans-isomerase Activity of Cyclophilin A: Cyclophilin A Protects . . . , The FASEB Journal, Aug. 7, 2002, 24 pages, express article 10.1096/fj.02-0060fje.

Christopher Hug et al., Diabetes, Obesity, and Acrp30/Adiponectin, BioTechniques, 2002, pp. 654-657, vol. 33, No. 3.

Albert Huisman et al., Anti-inflammatory Effects of Tetrahydrobiopterin on Early Rejection in Renal Allografts: Modulation of Inducible Nitric Oxide Synthase, The FASEB Journal, Jul. 2002, pp. 1135-1137. vol. 16.

Rok Humar et al., Hypoxio Enhances Vascular Cell Proliferation and Angiogenesis in Vitro Via Rapamyen (mTOR)-dependent Signaling, The FASEB Journal, Jun. 2002, pp. 771-780, vol. 16.

Shuji Isotani et al., Immunopurified Mammalian Target of Rapamycin Phosphorylates and Activities p70 S6 Kinase a in Vitro, The Journal of Biological Chemistry, No. 26, 1999, pp. 34493-34498, vol. 274, No. 48.

Richard S. Jope et al., AP-I and NF-kB Stimulated by Carbachol in Human Neuroblastoma SH-SY5Y Cells and Differentially Sensitive to Inhibition by Lithium, Molecular Brain Research, May 6, 1997, pp. 171-180.

Nathanael Larochette et al., Rapid Communication - Arsenite Induces Apoptosis Via A Direct Effect on the Mitochondrial Penneability Transition Pore, Experimental Cell Research 1999, pp. 413-421.

Ron Levy et al., Lidocaine and Muscimol Microinjections in Subthalamic Nucleus Reverse Parkinsonian Symptoms, Brain, 2001, pp. 2105-2118.

Gabriel T. Liberatore et al., Inducible Nitric Oxide Synthase Stimulates Dopaminergic Neurodegeneration in the MPTP Model of Parkinson Disease, Nature Medicine, Dec. 1999, pp. 1403-1409, vol. 5, No. 12.

Patricia Limousin et al., Electrical Stimulation of the Subthalamic Nucleus in Advanced Parkinson's Disease, The New England Journal of Medicine, Oct. 15, 1998, pp. 1105-1111.

John L. Lodge et al., Thiol Chelation of Cu2+ by Dihydrolipoic Acid Prevents Human Low Density Lipoprotein Peroxidation, Free Radical Biology & Medicine, 1998, pp. 287-297, vol. 25, No.3.

Jia Luo et al., Subthalamic GAD Gene Therapy in a Parkinson's Disease Rat Model, Science, Oct. 11, 2002, pp. 425-429, vol. 298.

W. S. Lynn et al., Neuroimmunodegeneration: D Neursons and T Cells Use Common Pathways for Cell Death, The FASEB Journal, Sep. 1995, pp. 1147-1156, vol. 9.

W. S. Lynn et al., Possible Control of Cell Death Pathways in Ataxia Telangiectasia, NeuroImmunoModulation, 1997, pp. 277-284.

William S. Lynn et al., Pathogenic Mechanisms in Neuroimmunodegeneration, Neuroimmunodegeneration, 1998, pp. 51-74, Chapter 3.

Antonio Macho et al., Gluthathione Depletion is an Early and Calcium Elevation is a Late Event of Thymosyte Apoptosis, The Journal of Immunology, 1997, pp. 4612-4619.

Norikazu Maeda et al., PPARy Ligands Increase Expression and Plasma Concentrations of Adiponectin, an Adipose-Derived Protein, Diabetes, Sep. 2001, pp. 2094-2099, vol. 50.

Michael J. Meredith et al., Expression of Bcl-2 Increases Intracellular Glutathione by Inhibiting Methionine-Dependent GSH Efflux, Biochemical and Biophysical Research Communications, 1998, pp. 458-463, vol. 248, No. 3.

Michael J. Meredith et al., Impaired Glutathione Biosynthesis in Culture Human Ataxia-Telangiectasia Cells, Cancer Research, Sep. 1, 1987, pp. 4576-4581.

Laurent Miccoli et al., Potentiation of Lonidamine and Diazepam, Two Agents Acting on Mitochondria, in Human Glioblastoma Treatment, Journal of the National Cancer Institute, Sep. 16, 1998, pp. 1400-1406, vol. 90, No. 18.

Laszlo Nagy et al., Oxidized LDL Regulates Macrophage Gene Expression through Ligand Activation of PPRAy, Cell, Apr. 17, 1998, pp. 230-240, vol. 93.

George Nickeing, et al., Redox-Sensitive Vascular Smooth Muscle Cell Proliferation Is Mediated By GKLF and ID3 in vitro and in vivo, The FASEB Journal, Feb. 2002, pp. 1077-1086, vol. 16.

C. Stefan I. Nobel, et al., Mechanism of Dithiocarbamate Inhibition of Apoptosis: Thio Oxidation by Dithiocarbamate Disulfides Directly Inhibits Processing of the Caspase-3 Proenzyme, American Chemical Society, 1997, pp. 636-643, vol. 10.

Jerrold M. Olefsky, Treatment of Insulin Resistance with Peroxisome Proliferator-Activated Receptor Agonists, The Journal of Clinical Investigation, Aug. 2000, pp. 467-472, vol. 106.

Amanda J. O'Neill, et al., Glutathione Depletion-Induced Neutrophil Apoptosis Is Caspase 3 Dependent, SHOCK, pp. 605-609, 2000, vol. 14, No. 6.

Noriyuki Ouchi, M.D., et al., Adiponectin, An Adipocyle-Derived Plasma Protein, Inhibits Endothelial NF-KB Signaling Through A Camp-Dependent Pathway, Circulation, Sep. 2000, pp. 1296-1301.

Erin K. Pias, et al., Apoptosis in Mitotic Competent Undifferentiated Cells is Induced by Cellular Redox Imbalance Independent of Reactive Oxygen Species Production, The FASEB Journal, Jun. 2002, pp. 781-790, vol. 16.

Luigi Ravagnan, et al., Lonidamine Triggers Apoptosis Via A Direct, Dcl-2-Inhibited Effect On The Mitochongrial Permeability Transition Pore, Stockton Press, Dec. 1998, pp. 2537-2546.

Maria E. Ryan, DDS, et al., Potential of Tetracyclines to Modify Cartilage Breakdown in Osteoarthritis, Current Opinion in Rheumatology, 1996, pp. 238-247.

Carolyn S. Sevier, et al., Formation and Transfer of Disulphide Bonds in Living Cells, Nature Reviews Molecular Cell Biology, Nov. 2002, pp. 836-847.

Stahl, et al., Insulin Causes Fatty Acids Transport Protein Translocation and Enhanced Fatty Acid Uptake in Adipocytes, Developmental Cell, Apr. 2002, pp. 477-488, vol. 2.

Lichiro Shimomura, Leptin Reverses Insulin Resistance and Diabetes Mellitus in Mice with Congenital Lipodystrophy, Nature, Sep. 1999, pp. 73-76, vol. 401.

Anatoly A. Starkov, Myxothiazol Induces $H_2O_2$ Production from Mitochondrial Respiratory Chain, Biochemical and Biophysical Research Communications, 1991, pp. 645-650.

Claire M. Steppan, et al., The Hormone Resistin Links Obesity to Diabetes, Nature, Jan. 2001, pp. 307-312, vol. 409.

Yuichiro J. Suzuki, et al., a-Lipoic Acid Is A Potent Inhibitor of NF-KB Activation In Human T Cells, Biochemical and Biophysical Research Communications, Dec., 1992, pp. 1709-1715, vol. 189.

Tiina M. Tikka, et al., Minocycline Provides Neuroprotection Against N-Methyl-D aspartate neurotoxicity by Inhibiting Microglia, The Journal of Immunology, 201, pp. 7527-7533, (No date available).

Davide Trotti, et al., Peroxynitrite Inhibits Glutamate Transporter Subtypes, The Journal of Biological Chemistry, Mar. 15, 1996, p. 5976-5979.

Stuart D. Tyner, et al., P53 Mutant Mice That Display Early Ageing-Associated Phenotypes, Jan. 2002, Nature, pp. 45-53, vol. 415.

A.F. Tsyb, Galavit in Experimental Tumor Therapy, International Journal of Immunorehabilitation, May 1999, pp. 398-403.

Shugo Udea, Redox Regulation of Caspase-3(-like) Protease Activity: Regulatory Roles in Thioredoxin and Cytochrome c1, The Journal of Immunology, 1998, pp. 6689-6695.

D.W. Voehringer, et al., Bcl-2 Expression Causes Redistribution of Glutathione to the Nucleas, Proceedings National Academy of Sciences USA, Mar. 1998, pp. 2956-2960, vol. 95.

Xiantao Wang, et al., Epidermal Growth Factor Receptor-Dependent Akt Activation By Oxidative Stress Enhances Cell Survival, The Journal of Biological Chemistry, May 2000, pp. 14624-14631, vol. 275.

Huafeng Wei, et al., Neuronal Apoptosis Induced by Pharmacological Concentrations of 3-Hydroxykynurenine: Characterization and Protection By Dantrolene and Bcl-2 Overexpression, Journal of Neurochemistry, Jul. 2000, pp. 81-90.

Andreas Weihofen, et al., Identification of Signal Peptide Peptidase, a Presenilin-Type Aspartic Protease, Science, Jun. 2002, pp. 2215-2218, vol. 296.

Roland H. Wenger, Cellular Adaptation to Hypoxia: O2-Sensing Protein Hydroxylases, Hypoxia-Inducible Transcrption Factors, and O2-Regulated Gene Expression, The FASEB Journal, Aug. 2002, pp. 1151-1162.

Michael S. Wolfe, et al., Intramembrane Proteases-Mixing Oil and Water, Science, Jun. 2002, vol. 296.

Paul K.Y. Wong, et al., ts1-MoMuLV: A Murine Model of Neuroimmunodegeneration, Neuroimmunodegeneration, 1997, pp. 30-35.

Paul K.Y. Wong, et al, Neuroimmunodegeneration Syndromes: Definition and Models, Neuroimmunodegeneration, 1998, pp. 29-50.

Du Chu Wu, et al., Blockade of Microglial Activation Is Neuroprotective In The I-Methyl-4-Phenyl-1,2,3,6-Tetrahydropyridine Mouse Model of Parkinson Disease, The Journal of Neuroscience, Mar. 1, 2002, pp. 1763-1771.

T. Yamauchi, et al., The Fat-Derived Hormone Adiponectin Reverses Insulin Resistance Associated with Both Lipoatrophy and Obesity, Nature Medicine, Aug. 2001, vol. 7.

Mingshan Yan, et al., The Ataxia-Telangiectasia Gene Product May Modulate DNA Turnover and Control Cell Fate by Regulating Cellular Redox in Lymphocytes, The FASEB Journal, May 2001, pp. 1132-1138, vol. 15.

Mingshan Yan, et al., Prevention of Thymic Lymphoma Development in Atm-/-Mice By Dexamethasone, Cancer Research, Sep. 2002, pp. 5153-5157.

Takafumi Tokota, et al., Adiponectin, A New Member of the Family of Soluble Defense Collagens, Negatively Regulates the Growth of Myelomonocytic Progenitors and the Functions of Macrophages, Blood, Sep. 2000, pp. 1723-1732, vol. 96.

Sang-Oh Yoon, et al., Selenite Suppresses Hydrogen Peroxide-Induced Cell Apoptosis Through Inhibition of ASKI/JNK and Activation of P13-K/Akt Pathways, The Faseb Journal, Nov. 2001.

Juha Yrjanheikki, et al., A Tetracycline Derivative, Minocycline, Reduces Inflammation and Protects Against Focal Cerebral Ischemia With A Wide Therapeutic Window, PNAS, 1999, 13496-13500, vol. 96.

Seong-Woon Yu, et al., Mediation of Poly (ADP-Ribose) Polymerase-1-Dependent Cell Death by Apoptosis-Inducing Factor, Science, Jul. 2002, vol. 297.

Naoufal Zamzami, The Thiol Crosslinking Agent Diamide Overcomes the Apoptosis-Inhibitory Effect of Bcl-2 By Enforcing Mitochondrial Permeability Transition, Oncogene, 1998, pp. 1055-1063.

Li Zhang, et al., pH-Induced Intramolecular Electron Transfer Between the Iron-Sulfur Protein and Cytochrome c1 in Bovine Cytochrome bc1 Complex, The Hournal of Biological Chemistry, Sep. 1999, pp. 7656-7661, vol. 11.

* cited by examiner

MODULATION OF CELL FATES AND ACTIVITIES BY DIKETO PHTHALAZINES

BACKGROUND OF THE INVENTION

Current treatments for human diseases target the disease and generally focus on eliminating the inciting agent or the symptoms, such as microbes, antigens, tumors, and pain, usually injuring healthy tissues in the process. Treatments that focus, instead, on enabling the host to treat its own disease, without toxic side effects, by supporting the host in controlling its cellular functions, are the subject of this invention, which methods of treatment comprise phthalazine dione compounds that buffer intracellular reduction and oxidation to modulate cell fates in various disease states.

In stressed cells with uncontrolled life and death cycles—as in neurodegenerative, autoimmune, hyperproliferative, hyperinflammatory, or iatrogenic diseases—the intracellular redox status deviates from its normal physiological state. In homeostasis, the intracellular redox status provides the proper environment for various cellular processes of growth, differentiation, activity, and death. An impaired or aberrant intracellular redox status, as it disables cellular processes, deprives cells of the ability to defend against stresses and therefore to survive. The maintenance of redox status is thus critical to the fate of the cell.

Any number of stresses greatly perturbs cellular redox status. Aberrant redox status results from internal causes such as defective regulatory gene products or from external causes such as radiation, chemotherapeutic agents, toxins, inflammogens, antigens, microbes, caloric excesses, oxidants, and carcinogens. As cellular redox agents become depleted during stress, cells inevitably dysfunction and die prematurely, as in Alzheimer's, AIDS, Huntington's, Parkinson's, ALS, psoriasis, and cancer.

Research has shown that alterations in cellular redox status play a role in cellular signaling, suggesting that antioxidants and sulfhydryl-reactive agents, which alter the redox status, could modulate cellular activation (see U.S. Pat. No. 5,994,402). Moreover, cellular thiols are known to be important in maintaining intracellular redox status (see U.S. Pat. No. 5,994,402). Consequently, altering the redox state of cells by depleting cellular thiol has been described as a method to reduce inflammation (see U.S. Pat. No. 5,994,402). This method, however, does not disclose use of any phthalazine compounds to maintain the cellular redox status.

Phthalazine compounds such as 5-amino-2,3-dihydro-1,4-phthalazinedione, also known as luminol, have been widely used in photothermographic imaging and in chemiluminescent labeling of cellular structures. However, their pharmacological or therapeutic use has been limited to identification as an inhibitor of poly (ADP-ribose) polymerase, an enzyme that responds to DNA damage (see U.S. Pat. Nos. 5,874,444; 5,719,151; 5,633,282), and to application in treating skin aging, Alzheimer's, atherosclerosis, osteoarthritis, osteoporosis, age-related macular degeneration, muscular dystrophy, immune senescence, viral infections, and cancer as diseases involving the functions of poly (ADP-ribose) polymerase (see U.S. Pat. Nos. 5,874,444; 5,719,151; 5,633,282).

Furthermore, although phthaloylhydrazide derivatives have been described as anti-inflammatory or anti-hypoxic agents for use in treating disorders such as ulcerative colitis, Crohn's, diffuse sclerosis, diarrhea, proctitis, hemorrhoids, anal fissures, dyspepsia, intestinal infection, proctosigmoiditis, skin irritation, and transplant rejection (see U.S. Pat. Nos. 5,543,410; 5,512,573), their role in modulating intracellular redox status and cell fates was not recognized.

Methods for correcting imbalances in cellular redox status with currently available redox agents—cysteine, reduced thiols, antioxidants, reduced lipoates, and glucocorticoids—remain inadequate, in that these agents are labile, quickly oxidized, or unable to translocate to the proper region of the cell. Redox agents that buffer cellular redox imbalances, without toxicities, and thus enable redox-stressed cells to regain control over their redox status and defense mechanisms, would be beneficial in treating diseases accompanied or marked by impaired or aberrant intracellular redox status.

SUMMARY OF THE INVENTION

As adjunctive support therapy for stressed cells, regardless of the stress and its disease symptoms, phthalazine diones buffer and maintain intracellular redox potentials at any desired level, depending on dosage. Phthalazine diones may be used to correct redox imbalances and to thus support the host in a variety of disease states, including retroviral infections, hyperproliferation such as cancer, chronic and acute inflammation, autoimmunity, hypoxia, and regulatory gene deficiencies that perturb redox status, such as ataxia telangiectasia, trichothiodystrophy, amyotrophic lateral sclerosis, xeroderma pigmentosum, Cockayne syndrome, Huntington's, Parkinson's, and Alzheimer's.

DETAILED DESCRIPTION

The present invention discloses the use of phthalazine diones in conjunction with reduced thiol compounds to treat stressed hosts with diseases involving impaired or aberrant intracellular redox states. By buffering redox imbalances, phthalazine dione compounds reversibly modulate cellular functions, upregulating mitochondrial aerobic metabolism when the stressed cell needs energy to defend or repair, down-regulating metabolism when the stressed cell is overactive. Phthalazine diones thus modulate proliferation, secretion, differentiation, transformation, migration, and apoptosis rates, without toxic effects on non-stressed cells.

In mitochondrial aerobic metabolism, electron flow is fragile and easily perturbed by oxidant stresses. In times of stress, the cell must rapidly increase both the electron flow and the subsequent membrane proton ($H_+$) gradient. However, the electron flow and proton gradient may fail if overactivated or stressed. Electrons are then diverted directly to oxygen ($O_2$), producing toxic superoxide ($O_2^-$), while the proton gradient declines, hindering ATP production. Moreover, under the oxidant stress, mitochondrial membrane channels and permeability pores become oxidized, which distorts the channels and opens the pores. Consequently, protons, substrate anions, glutamate, reductants, cytochrome c, and nucleotides all leak through the distorted channels and opened pores, leaving the mitochondria and cell deficient in essential substances, energy, and redox status.

In a preferred embodiment of the invention, amino phthalazine diones are used to either facilitate or inhibit electron flow in mitochondria, and thus control ATP production. The effect of amino phthalazine diones varies according to the dosage used, the amount of reduced thiol substrates in the cell, and the state of oxidation of the amino phthalazine dione. The phthalazine diones of the present invention are preferably incorporated into pharmaceutical forms suitable for administration by oral, rectal, transdermal, or parenteral routes, including subcutaneous, intramuscular, intravenous, and intradermal, and preferably include pharmaceutically acceptable carriers, adjuvants, or stabilizers as is well known to the skilled in the art.

In general, a therapeutically effective amount or dose of a compound of the invention, sufficient to ameliorate the disease symptoms, will depend on the acuteness of the disease, particular deficiencies or redox status of the host, and developmental condition of the stressed cell, but will be in the range of 2–10 mg per kg of body weight. In vitro, at the low dose of 20–50 [M, amino phthalazine diones facilitate electron flow at mitochondrial Complex III, thereby increasing ATP production, DNA synthesis, and cell cycling. At an intermediate dosage of 100 µM, amino phthalazine diones slow down electron flow, with concomitant effects on ATP production, DNA synthesis, and cell cycling, so that differentiation can proceed. At the high dose of 200 µM, amino phthalazine diones completely stop ATP production, DNA synthesis, and cell cycling in the stressed cell, but the cell does not die.

Thus, amino phthalazine diones may be used to control cell fates and act by serving as a redox buffer for the redox- and thiol-sensitive energy producing pathways in the mitochondrion, signaling pathways at the cell plasma membrane, and glutamate uptake and cytokine secretion by astrocytes in the central nervous system (see Trotti et al., *J. Biol. Chem.* 271: 5976–5979, 1996). In addition, amino phthalazine diones catalyze disulfide cross-linkages in the adenine nucleotide translocase (ANT) of the mitochondrial anion channels and in the megapores, which prevents energy production, increases production of the potent signal transducers hydrogen peroxide ($H_2O_2$) and superoxide ($O_2^-$) (see Zamzami et al., *Oncogene* 16: 1055–1063, 1998; Constantini et al., *J. Biol. Chem.* 271: 6746–6751, 1996), and liberates the apoptosis-inducing factors cytochrome c and AIF.

Under any stress, redox status is inevitably impaired as aerobic metabolism is necessarily overworked. Any stress to the cell, especially if prolonged, will deplete the cell of redox agents, including thiols, glutathione, thioredoxins, iron-sulfur proteins, cysteine, and thio]proteins, as well as redox-sensitive proteins such as catalase. Chronic stress leads to cellular and organelle thiol deficiencies, as blood cysteine is very limited. In turn, since many cellular pathways are controlled by or depend on intracellular redox activities, thiol deficiencies lead rapidly to impaired energy production, with increased oxidant production and progressive mitochondrial and cell death.

With prolonged thiol deficiencies, replacement therapy with available thiols is difficult and usually inadequate. Cysteine and other reduced thiols are labile and rapidly oxidized to toxic metabolites in the presence of oxygen. Most antioxidants, which dissipate oxygen-based oxidants, are unable to penetrate to the electron-transporting inner mitochondrial membrane to modulate the iron-sulfur protein mediated electron flow in mitochondrial Complex III or to stabilize disulfide cross-linkages that control permeability of the mitochondrial megapores and channels. Antioxidants also cannot supply the cysteine required in manufacture of most proteins or the energy required to combat the chronic stresses or repair the cellular damages.

In particular, under certain conditions, loss of redox control may cause:

(1) cross-linking of thiols in the adenine nucleotide translocase and other proteins, which then opens the mitochondrial transmembrane pores and channels and leads to a decline in mitochondrial voltage and energy production (see Constantini et al., *J. Biol. Chem.* 271: 6746–6751, 1996; Larochette et al., *Exp. Cell Res.* 249: 413–421, 1999; Zamzami et al., *Oncogene* 16:1055, 1998);

(2) increases in intracellular calcium levels;

(3) activation of redox defenses and heat shock proteins;

(4) activation of redox-sensitive cell cycling factor AP-1 and E2F/Rb pathway;

(5) activation of apoptotic pathways via AsK-1, with liberation of caspases, cytochrome c, and AIF from the failing mitochondria;

(6) a decline in ADP-dependent electron flow, as well as alteration of mobility of redox sensitive iron-sulfur proteins at mitochondrial Complex III (see Zhang et al., *J. Biol. Chem.* 275: 7656–7662, 2000);

(7) oxidation of macromolecules, including redox-sensitive proteins such as glutamate transporters (see Trotti et al., *J. Biol. Chem.* 271: 5976–5979, 1996), mitochondrial DNA, and membrane lipids;

(8) a failure in modulation of redox-sensitive phosphatases PTB-1, SHP-1, and SHP-2 (see Doza et al., *Oncogene* 17: 19–26, 1998); and (9) dysregulation of the thiol-sensitive MAP kinase-Ras pathway, which controls cellular proliferation.

With redox support to alleviate the redox stress and restore or buffer the redox status, the mitochondria resumes energy production. The cell then repairs stress-induced damages, restocks essential substrates, and removes all offenders, in essence curing its own disease. Any external therapist, to be successful, must therefore enable the cell to correct the redox aberration, remove the cellular stress, and repair mechanical damages—without toxic side effects. Accordingly, in a preferred embodiment of the invention, phthalazine diones primarily support metabolically stressed cells in a host, without toxic effects, by buffering intracellular redox status, rather than treat a particular disease.

Redox support therapy is crucial in various disease states, as in:

(1) syndromes in which overactive inflammatory cells, lymphocytes, macrophages, astrocytes, or microglia greatly stress both redox defenses and energy production, as in chronic inflammatory processes in arteries (atherosclerosis), in brain (Parkinson's, Alzheimer's, Huntington's, MS, AIDS), in gut (duodenal ulcer, ulcerative colitis, chronic hemorrhoids), in chronic viral infections in T cells or liver, in skin (psoriasis, leprosy, burns), and in regulatory gene defects such as ataxia telangiectasia, trichothiodystrophy, and p53 or SOD excess; and (2) syndromes of rapid cell proliferation or clonal expansion, in which electron flow between iron-sulfur proteins and cytochrome $c_1$ in mitochondria is persistent or uncoupled.

To survive the stress, the cell must replace its deficient thiols and maintain optimum mitochondrial redox potentials and activities. In a preferred embodiment of the invention, therapy includes treating the host with mixtures containing cysteine, acetyl cysteine, glutathione, and alpha lipoic acid to replace thiols. In addition, a therapeutically effective amount or dose of an amino phthalazine dione is administered to stressed cells, to maintain the desired redox status and mitochondrial energy production, as well as the redox-sensitive MAP kinase-Ras PT3K signal transduction pathways.

The amount of amino phthalazine dione needed or effective at any one point is cell- and stress-dependent. Optimum dosage and treatment require proper diagnosis of the thiol redox status of the host's aerobic metabolism in the stressed mitochondria, as well as administration sufficiently early on in cell or stress development. The thiol redox status must also be frequently monitored, since amino phthalazine diones are oxidatively very labile and rapidly expended. In a preferred embodiment of the invention, the amino phthalazine dione is administered in the presence of an oxidative protector such as glutathione.

In tissue culture, small doses of less than 1 μg/ml of amino phthalazine diones are effective for conditions with chronic losses of cells, especially of stem or developing cells, as in neuroimmuno-degenerative syndromes. In conditions where proliferation and apoptotic rates are out of control, including cancer, autoimmunity, infection, and traumas, in tissue culture, doses greater than 50 μg/ml of amino phthalazine diones are required. Successful treatment with the phthalazine dione compounds of the invention therefore depends both on redox diagnosis with repeated assessment of cellular thiol redox status and on maintenance of proper dosage of the compound over time. Treatment with phthalazine diones is directed at cells or organs in which stress has dysregulated thiol redox homeostasis, with energy deprivation and oxidant stress.

In a preferred embodiment of the invention, amino phthalazine diones also act as efficient substrates for reaction with many of the reactive oxygen species and radicals that are inevitably generated in the stressed mitochondria. Because of antioxidant, redox-buffering, anti-inflammatory, antiproliferative, non-toxic, and immunomodulatory properties, phthalazine diones are beneficial as adjunctive support therapy for the stressed cell regardless of the compromising stress or its downstream symptoms. In rare disease states, redox support may be sufficient for the diseased cell to cure itself, but in some situations, the cell will also need the mechanical, pharmacological, or genetic support of conventional medical and nutritional therapies. The therapeutic methods of this invention should thus be used in combination with standard therapies for treating particular disease conditions. The following examples further illustrate the invention.

EXAMPLE 1

Uncontrolled Inflammation

In inflammatory conditions, such as acute infections, wounds, and immune responses, phthalazine diones, especially amino phthalazine diones, quickly ameliorate the painful redox-induced edematous swelling and facilitate rapid healing. Edematous inflammatory lesions in intestines, such as duodenal ulcers, ulcerative colitis, and acute vascular injury, are all suppressed to some degree by thiol redox modulators, including dihydrolipoates, reduced biopterins, amino phthalazine diones, and more slowly by glucocorticoids. Healing rates increase, with replacement of the injured epithelial cells by thiol redox-stimulated new cell growth. Thus, phthalazine diones, acting as thiol redox modulators, suppress injurious over-reactive inflammatory responses and also facilitate healing and replacement of injured cells.

EXAMPLE 2

Uncontrolled Proteolysis

In conditions with aberrant or uncontrolled proteolysis, as in apoptosis or necrosis, thiol redox modulators, especially thioredoxin, either upregulate or downregulate the regulatory proteases involved in processing and digesting the thiol redox dependent caspases, endonucleases, and histone deacetylases responsible for protein and DNA hydrolysis. Diamide, a phthalazine dione with activity similar to the oxidized 4-amino phthalazine dione, can activate and cross-link proteases that hydrolyze procaspase 3 to the active caspase fragments that, along with cytochrome c, initiate the apoptotic cascade in the nucleus.

Since these cross-linking agents can also oxidize essential membrane proteins, such as the adenine nucleotide translocase in mitochondria or amyloid protein fragments in brain, the result is membrane pore formation in mitochondria with increased reactive oxygen species and cell destruction (see Ueda et al., *J. Immunol.* 161: 6689–6695, 1998). Thus, reduced phthalazine diones can up- or down-regulate redox-sensitive proteases and thereby dictate life and death of stressed proliferating cells.

EXAMPLE 3

Helicase Deficiencies

The XPD gene of the xeroderma pigmentosum family codes for a helicase. In XPD deficiency, DNA transcription and repair functions are impaired, resulting in multiple symptoms of early aging (see De Boer et al., *Science* 296: 1276–1281, 2002).

Wasting, loss of subcutaneous fat and muscle cells, gray brittle greasy hair with hyperplasia of sebaceous and mammary glands, severe osteoporosis, atrophic germ and stem cells, and immuno-neurodegenerative and hyperplastic changes all occur prematurely in XPD-deficient mice or humans.

The failure to maintain normal numbers of cells or normal amounts of cellular thiols, at least in the brittle hair, suggests that a global thiol redox deficiency is responsible for the progressive wasting and chronic cell losses. Since amino phthalazine diones with reduced thiol redox modulators, at low dosage, stimulate cell growth and maintain thiol redox status in cells, treatment with appropriate amounts of reduced thiol redox modulators plus the phthalazine diones of the present invention will likely prevent the premature aging in regulatory gene deficiencies such as XPD deficiency.

EXAMPLE 4 p53 and Aging

In conditions where cell growth and tumor formation are constantly suppressed by growth suppressor genes like p53, signs of premature aging and replication senescence appear early (see Tyner et al., *Nature* 415: 45–50, 2002). Chronic cell losses in skin, hair, bone, adipose tissue, and the immune system occur. The p53 protein is a potent transcription factor that suppresses cell growth and DNA synthesis and is also an activator of genes that induce oxidative stress and apoptosis, such as Bax and caspases 3 and 9.

Thiol redox modulators such as phthalazine diones, which maintain cellular replication pathways by modulating cellular redox status, override the p53-induced suppression and maintain a balanced between apoptotic or proliferation pathways, depending on dosage. Data to support this homeostatic concept for thiol redox modulators in p53-induced aging are under evaluation. Since thiol redox modulators beneficially balance rates of cell death and proliferation in other syndromes of premature aging, including XPD deficiency and retrovirus-induced degenerative diseases, it is likely that thiol redox modulators, at appropriate dosages, can re-balance the p53-induced thiol redox potential and thereby prevent the degenerative sequela.

EXAMPLE 5

Retroviral-Induced Redox Imbalance

Oncogenic retroviral infections such as HIV in humans or MOMU-LV-Ts1 in mice cause degenerative changes with severe losses of brain cells, immune cells, and germ cells. Other cells like astrocytes and microglia in brain become activated, secrete nitric oxide (NO) and superoxide ($O_2^-$), and grow and accumulate excessively. This imbalance in cell growth and death rates eventually leads to fatal immune and neuronal deficiency syndromes with subsequent transformation in some cells.

In mice infected at 2 days of age with the Ts1 virus, hind limb paralysis occurs with severe wasting, especially of immune organs. In humans infected with HIV, severe immune deficiency with sensory and motor neuropathy also results. In these wasting syndromes with disordered life and death pathways in various cells, some therapeutic attempts with thiol redox modulators other than amino phthalazine diones have been partially successful (see Lynn and Wong, *Neuroimmunomodulation* 4: 277–284, 1997; Yan et al., *FASEB J* 15: 1132–1138, 2001). In these studies, phthalazine diones plus thiol redox modulators appear to be sufficient to maintain survival and an adequate intracellular thiol redox potential in brain and in thymus.

Since retroviruses activate caspase-dependent apoptosis, and since thiol redox modulators, oxidized and reduced, regulate caspase production from procaspases (see Nobel et al., *Chem. Res. Toxicol.* 10: 636–643, 1997), thiol redox modulators in mitochondria, especially an amino phthalazine dione plus dexamethasone, will likely prevent both the loss and the hyperplasia of cells dysregulated by the viruses. Experiments using various thiol redox modulator regimens as preventative therapy in Ts1-infected mice are currently underway.

EXAMPLE 6

Polyglutamine Model

In disease states where aberrant peptides slowly accumulate in the brain, early neuronal death with glial hypertrophy occurs. In Huntington's disease, polyglutamine sequences or tracts accumulate in the huntingtin protein. These tracts bind to and inhibit transcription complexes containing Sp-1 and TAFII130 coactivators. Transcription rates decrease, and dysregulated neurons slowly die, first in the caudate nucleus and later in the hippocampus.

Non-proliferating, non-replaceable neurons usually die from metabolic redox imbalances, rather than from programmed death. Therefore, neuronal death in Huntington's is likely to be redox-mediated and induced by activation of redox-sensitive cytokines, metalloproteases, and reactive oxygen species (ROS) by activated migroglia and astrocytes (see Chen et al., *Nature Med.* 6: 797–801, 2000). In that case, reduced thiol redox modulators, which at low doses promote cell growth and longevity in redox-suppressed cells, should prove to be useful therapy (see Dunah et al., *Science* 296: 2238–2243, 2002).

In other neurodegenerative syndromes in which aberrant peptides accumulate, including Alzheimer's and Parkinson's, presenilin or synucleins may be responsible for accumulation of the Lewy bodies and B-amyloid peptides. Accumulation of these hydrophobic peptides in plasma, mitochondrial, or endoplasmic reticulum (ER) membranes of the cell may be responsible for the neuronal losses in these syndromes. These toxic peptides, like the polyglutamine proteins in Huntington's, also lead to astroglia-induced imbalances in thiol redox metabolism, with cell swelling, membrane leakiness, and mitochontrial necrosis. Maintenance of thiol redox status with reduced thiol redox modulators, especially an amino phthalazine dione and cysteine, should prevent or delay the neuronal death in these degenerative diseases (see Wolfe and Selkoe, *Science* 296: 2156–2157, 2002; Welhofen et al., *Science* 296: 2215–2218, 2002).

EXAMPLE 7

NMDA-Induced Excitotoxicity Model

In NMDA-induced neuronal excitotoxicity, secreted microglial inflammatory products—glutamate, quinolinic acid, inflammatory cytokines, tumor necrosis factor, 1L-1B, superoxide ($O_2^-$), and nitric oxide (NO)—are likely responsible for the neuronal necrosis (see Tikka and Kolstinaho, *J. Immunol.* 166: 7527–7533, 2001). These excitotoxins all rapidly perturb redox homeostasis in neurons, which slowly die, and in activated astroglia, which become activated and proliferate.

Minocycline, a cyclic polyhydroxy ketonic amide, which suppresses mitochondrial activity, prevents both the NMDA-induced proliferation of and toxic secretions by activated astrocytes, as well as the subsequent neuronal death (see Tikka and Kolstinaho, *J. Immunol.* 166: 7527–7533, 2001). This suggests that cell death in neurons, secretory proliferative activation of astroglia, and proliferative response in astrocytes in the spinal cord are mitochondrial redox-mediated and that correction of thiol redox status by phthalazine diones should be able to control the fate of these brain cells.

EXAMPLE 8

Premature Aging with Cancer Models

In regulatory gene-dependent syndromes of premature aging, including ataxia telangiectasia, Down's, trichothiodystrophy, Bloom's, p53 over-activity (see De Boer et al., *Science* 296: 1276–1281, 2002; Tyner et al., *Nature* 415: 45–50, 2002), in which life and death of specific cell types are aberrant, appropriate treatments in vitro and in vivo with thiol redox modulators have been partially successful. In ataxia telangiectasia gene (ATM) deficiency in mice, early pretreatment with dexamethasone, the glutathione secretagogue, completely prevents the excessive proliferation and development of the fatal thymic cancer.

Other thiol redox modulators, such as N-acetyl cysteine and dehydrolipoic acid, also delay the premature degeneration of cells and the thymomas. Thiol redox modulators also correct the delayed differentiation and excessive production of DNA in ATM-deficient lymphoid cells (see Yan et al., *FASEB J* 15: 1132–1138, 2001; Lynn et al., unpublished). However, in the ATM-deficient mice, treatment was fully successful only if the thiol redox modulators were applied early, before two weeks of age and before tumor development.

Dexamethasone alone completely prevents tumor formation if given to 10-day old ATM-deficient mice for three weeks, but does not suppress tumor growth or increase longevity if given at physiologic doses at three months of age. Whether amino phthalazine diones with other thiol redox modulators, which suppress growth of non-transformed ATM-deficient cells in vitro, can fully suppress tumors in vivo, without toxicity, has not been rigorously evaluated. Cross-linking redox modulators such as diamide, menadione, and oxidized phthalazines are known to stop cell growth, activate caspases, and initiate apoptosis in some tumor cells (see Pias and Aw, *FASEB J* 16: 781–790, 2002).

EXAMPLE 9

Oxygen-based Model

In acute metabolic distress, as in hypoxia, redox-sensitive transcription factors such as HIFA are rapidly activated, or under-activated if the oxygen deprivation is not too severe. These transcription factors are triggered by the alternate redox-sensitive mammalian target of rapamycin (mTOR) signal transduction pathway, which is upregulated by low oxygen, ATP, and amino acids. Activated mTOR markedly upregulates DNA synthesis and cellular proliferation, especially in endothelial and vascular smooth muscle cells. Consequently, mTOR is involved in many redox-sensitive proliferative diseases of vascular tissues, including diabetic retinopathy, psoriasis, rheumatoid arthritis, certain tumors, and arteriosclerosis (see Humar, *FASEB J.* 16: 771–780, 2002).

Whether mTOR or its upstream activators are redox sensitive is not clear. Nonetheless, oxygen at low dose, like amino phthalazine diones at low dose, increases proliferation, whereas oxygen at very low dose (<1%), or phthalazines at high dose, stop proliferation and activate cell death pathways. Vascular cell fates are clearly dependent on external redox agents that modulate internal redox status, and the responses and fates of these cells are readily controlled in a dose-dependent manner by external redox agents such as oxygen, amino phthalazine dione, diamide, or permeant thiols, which modulate the mTOR-signaling pathway. These redox agents should therefore be useful as redox buffers in controlling the redox-sensitive mTOR pathway, ameliorating various vascular proliferative inflammatory diseases, and controlling angiogenesis both in tumor growth and inflammatory syndromes, particularly in brain.

EXAMPLE 10

Uncontrolled Oxygen Models

In uncontrolled oxygen metabolism, oxygen is not fully reduced, such that reactive oxygen intermediates accumulate. Cell fate is highly dependent on the concentration, location, and longevity of reactive oxygen species such as $O_2^-$, $H_2O_2$, OH., NO, and OHOO.. In proliferating vascular smooth muscle cells, addition of $O_2^-$ or $H_2O_2$ quickly increases DNA synthesis, via activation of the Id3/E2F pathway. In the presence of iron plus $H_2O_2$, which produces the more potent OH. radical, DNA synthesis, Id3 protein, and Id3 mRNA rapidly decline, while cell death rates increase. Thus, the fate of growing smooth muscle cells is highly dependent on oxygen redox status.

The two oxygen redox-sensitive genes, Id3 and GKLF, which are differentially responsive to oxygen redox status, are most sensitive to rapid changes in concentrations of reactive oxygen species. With increased concentrations in OH., Id3 expression is downregulated, GKLF expression is upregulated, and DNA synthesis ceases (see Nickenig et al., *FASEB J.* 16: 1077–1086, 2002). The GKLF protein, when oxidized, is activated and inhibits Id3 expression by binding to the Id3 promoter. The Id3 protein, when reduced, is activated and upregulates the E2F-controlled proliferation pathway.

Thus, oxygen redox status, like thiol redox status, is a potent regulator of cell fates. Moreover, the two redox pathways, and the two electron acceptors oxygen and sulfur, interact repeatedly. For example, reduced phthalazines or thiols chemically reduce most of the reactive oxygen species, including peroxynitrite ($ONOO^-$). Tetrahydropterin ($BH_4$), a major cellular reductant in the central nervous system, reduces reactive oxygen species and the inducible oxidase iNOS. Under redox stress, in the presence of tetrahydropterin, iNOS produces nitric oxide (NO). Under redox stress when tetrahydropterin or reduced thiols are limited, iNOS produces superoxide ($O_2^-$). In turn, superoxide ($O_2^-$) or hydrogen peroxide ($H_2O_2$) activates Id3 and the E2F-controlled DNA synthesis pathway but only in the absence of iron or copper (see Dehmer et al., *J. Neurochem.* 74: 2213–2216, 2000; Husman et al., *FASEB J* 10: 1135–1141, 2002; Liberatore et al., *Nature Med.* 5: 1403–1409, 1999).

Thus, intracellular redox homeostasis, whether oxygen- or thiol-mediated, is dependent on concentrations of cellular reductants—tetrahyropterin, glutathione, cysteine, NADPH—and cellular oxidants—$O_2^-$, $H_2O_2$, NO, OH., $Fe^{3+}$—as well as on concentrations of permeant extracellular reductants—reduced thiols, tetracyclines, phthalazines—and permeant extracellular oxidants—$O_2^-$, gamma radiation, doxorubicin, glucocorticoids, cis-platinum, doxirubicin, etc. Consequently, redox homeostasis can be readily maintained by appropriate doses of permeant redox agents, notably by phthalazine diones, and with protean therapeutic implications. Phthalazines, tetracyclines, or thiols (see Tikka and Kolstinaho, *J. Immunol.* 166: 7527–7533, 2001) potentially dictate and control the cell fate in activated or stressed cells, whether the disease-inducing redox imbalance is oxygen- or sulfur-mediated. In addition to controlling proliferation and activation pathways, these redox modulators also scavenge destructive oxygen radicals and thereby prevent apoptotic and necrotic pathways.

Potential therapeutic usefulness of these redox modulators in astroglia induced neurodegenerative diseases (see Tikka and Kolstinaho, *J. Immunol.* 166: 7527–7533, 2001), in renal allografts (see Husman et al., *FASEB J* 10: 1135–1141, 2002), and in inflammation-induced cell damages (see Ryan et al., *Curr. Opinion in Rheumatology* 8: 238–247, 1996) are now being recognized. Thus, redox modulating compounds, especially phthalazines, that modulate both the oxygen and sulfur redox pathways are proving to be therapeutically useful in situations where the host's redox mechanisms are out of control.

EXAMPLE 11

Chronic Inflammation Model with Accumulation of Excess Lipids

In situations where foreign fats such as oxidized fatty acids or cholesterol accumulates, a chronic inflammatory reaction ensues. Signaling and transport processes in lipid-laden membranes falter. Lipid-laden activated macrophages accumulate. Oxidant stress follows, due to deficiency in glucose transport in the lipid-laden membranes and the increased production of oxidants and proteases by the influx of activated macrophages. Chronic localized abscesses form. In vascular tissue, atherosclerosis with occlusive diseases, stroke, myocardial infarction, cystic mastitis, wet macular degeneration, and engorged activated adipocytes are the result. In all these syndromes, thiol redox homeostasis becomes gravely perturbed and cellular redox damage occurs. Syndrome X with insulin resistance (see Example 15) is an early sequela.

Therapies known to modulate the above lipid- and redox-induced syndromes include:
(1) thiol redox modulators, especially amino phthalazine diones, to buffer the aberrant thiol redox status;
(2) anti-proteases, especially minocycline, to block the excess proteolytic activity and suppress $O_2^-$ production by the induced NO synthase by macrophages;
(3) peroxisome proliferators, to accelerate oxidation of accumulating lipids;
(4) caloric restriction, to block input and accumulation of the aberrant lipids and $O_2^-$;
(5) glucocorticoids, to deplete thiols by excretion, inhibit growth, and accelerate death of the overactivated macrophages and microglia; and
(6) sepiapterin, to prevent superoxide ($O_2^-$) production by iNOS in the brain and to prevent activation of the apoptosis stimulating kinase AsK-1, especially in the brain.

Many external therapies are therefore available to modulate and prevent the chronic abscess formations induced by accumulation of aberrant oxidized fats in cell membranes. To fully maintain optimum redox status, over time, in disease states with differing etiologies, various combinations and doses of all six redox approaches may be required. With optimum redox support, the host will repair most damages and induce the means—for example, peroxisome proliferator receptors (PPARs) and adiponectin—to remove the offending fats. In severe defects, specific anti-proteases and antioxidants as those listed above are essential for optimal therapy.

EXAMPLE 12

Redox-Controlled Neuronal Survival

Oxidizing agents such as $H_2O_2$, NMDA agonists, and N-nitrosoguanidines rapidly kill primary neurons. In the presence of oxidants the redox-sensitive nuclear poly (ADP-ribose) polymerase, which cleaves $NAD^+$ to ADP-ribose and stabilizes nuclear proteins by ADP-ribosylating them, is rapidly activated. This depletes the neuron of $NAD^+$ as well as the reductants NADH and NADPH. This also rapidly facilitates nuclear uptake of the mitochondrial redox-sensitive flavoprotein, apoptosis inducing factor (AIF).

These oxidants also open the redox-sensitive permeability transition pores and anion channels in mitochondrial membranes, which release AIF. AIF is then taken up by the poly (ADP-ribose) polymerase-activated nucleus to initiate chromatin condensation. Chromatin condenses, mitochondria grow swollen, and mitochondrial processes become uncoupled. Mitochondria then produce more oxidants, $O_2^-$ and $H_2O_2$, and produce less ATP. In addition, the oxidants rapidly induce reshuffling of plasma membrane ionic phospholipids with surface exposure of phosphatidyl serine. This rapidly alters permeability and transport activities in plasma, mitochondrial, ER, and nuclear membranes. The plasma and ER membranes leak calcium, which activates innumerable signal transduction pathways, including ATM, mTOR, and p38 MAPK (see Yu et al., *Science* 297: 259–263, 2002; De Giorgi et al., *FASEB J* 10: 607–609, 2002).

Thus, redox status of most cellular membranes is rapidly altered by brief exposure to permeant oxidants, and cell death rapidly ensues, through both apoptotic (nuclear) and necrotic (plasma membrane) changes. Membrane-permeant reductants, such as phthalazine diones plus reduced biopterins and thiols, should be able to buffer and maintain the proper redox status in membranes of oxidant-stressed organelles as occurs in acute neurodegenerative syndromes such as hypoxia or glucose deficient states, or in chronic inflammatory states such as Parkinson's, Alzheimer's, ALS, MS, ataxia telangiectasia, or aging.

EXAMPLE 13

Role of Thiol Redox Status in Mitochondrial Activities

The major source of chemical energy and heat in aerobic cells is mitochondria. The modulatable permeable pores and channels in mitochondria are exquisitely sensitive to thiol redox status. The specific mitochondrial channel is composed of two thiol redox-sensitive proteins located in the inner membrane—adenine nucleotide translocase (ANT) and voltage dependent anion channel (VDAC)—and other coproteins such as cyclophilin D, hexokinase, benzodiazepine receptors, and the Bcl-2/Bax family of peptides. These proteins together control the permeability and transport of mitochondrial transmembrane channels and pores, which control ADP entry, proton exit, electron flow, intracellular calcium concentration, and $O_2^-$ production.

Bax, benzodiazepine receptors, and hexokinases, which bind to the outer membrane of mitochondria, regulate transport and pore formation in these membranes. Major physiologic modulators of this mitochondrial transmembrane pore include:
(1) transmembrane voltage, which is generated by electron and proton gradients;
(2) inducible membrane proteins, Bcl-2 and Bax; and
(3) thiol redox status, the redox state of Cys-56 on the channel protein ANT being a major regulator of the permeability of mitochondrial transmembrane pores (see He and Lemasters; *FEBS Letters* 512: 1–7, 2002).

Thiol oxidants or cross-linking agents such as diamide or diethyl maleate distort and open mitochondrial pores and channels, and uncouple electron flow, allowing oxygen to trap electrons and produce $O_2^-$, $H_2O_2$, and other radicals. Energy production declines, and mitochondria release cytochrome c, caspases, and AIF. Destructive cytochrome c, redox-sensitive proteases, and caspases are activated in the cytoplasm and the nucleus, causing cell death, both apoptotic and necrotic.

Reduced thiols, dithiothreatol, glutathione, N-acetyl cysteine, or agents such as Bcl-2, Bongkrekic acid, cyclosporine A, or chaperone cyclophilins that can stabilize ANT sulfhydryls and maintain pore permeability status can completely prevent the electron leak and the cell death (see Armstrong and Jones, *FASEB J* 16: (online), Jun. 7, 2002; Castantini et al., *Oncogene* 19: 307–314, 2000; Hong et al., *FASEB J* 16: 1633–1636, 2002). Whether permeant reductants such as the phthalazine diones of the present invention, which stabilize and maintain thiol redox status, alone stabilize the thiol redox-sensitive mitochondrial transmembrane pore in vivo is currently under investigation.

Under oxidant stressed conditions, including radiation, chemotherapy, occlusive vascular diseases, leptin-deficient or resistin-induced obesity, caloric excesses, and Type II Diabetes, in which optimal thiol redox status is not maintained by the diseased adipose tissue of the host, therapeutic support by external thiol redox buffers will be acutely necessary, at least until the host can repair and buffer the stressed and imbalanced thiol redox status and fully activate its hypoxia-inducible transcription factors (see Wenger, *FASEB J.* 16: 1151–1162, 2002; De Giorgi et al., *FASEB J.* 10: 607–609, 2002).

Depending on the type of oxidative stress, labile vicinal cysteinyl residues on ANT undergo cyclic oxidation, ionization, and eventually cross-linking. These oxidations and cross-linkages of protein thiols greatly perturb channel functions, especially by thiol cross-linking cyclic amines, diazenes (diamide), or phenylarsines. Uptake of ADP fails, protons are released with collapse of the inner membrane potential, ordered electron flow at mitochondrial Complex III falters, and $O_2$ now accepts the fluxing electrons with production of $O_2^-$ and other radicals. The oxidant-producing mitochondria release cytochrome c and AIF, and downstream oxidation of $NF_KB$, AP1 (major transcription factor for proliferation), AsK-1 (apoptosis stimulating kinase), glutathione, Bax, HDAC (histone deacetylase in nucleus), PTEN (phosphatase in cytoplasm), and ATM occurs. Apoptosis, senescence, quiescence, or necrosis results, depending largely on the extent and duration of the redox stress.

A photoactive diamine fluorescent cation, tetramethyl-rhodamine, which accumulates in mitochondria and releases free radicals when photoactivated, is a potent agonist of the mitochondrial transmembrane pore. When tetramethyl-rhodamine is activated, all downstream effects of oxidation and cross-linking of ANT's labile cysteinyl residues occur, including translocation and polymerization of Bax in mitochondrial membranes. These effects are fully inhibited by Bongkrekic acid, a specific inhibitor of mitochondrial transmembrane pores (see De Giorgi et al., *FASEB J.* 10: 607–609, 2002), as well as by reduced thiols, reduced phthalazines, cyclophilins, and pterines.

These observations suggest that the fate of cells under stress is largely dictated by mitochondrial thiol redox status, and that host and cell fates are readily buffered or controlled by permeant lipophilic redox-sensitive amines, such as phthalazine diones, tetrahydrobiopterin, and permeant thiols.

EXAMPLE 14

Thiol Redox Status in Mitochondria in Cancer Treatment

Controlling entry and exit of small molecules—$Ca^{2+}$, $H^+$, $O_2^-$—and substrate anions through the redox—and voltage-sensitive mitochondrial channels and pores is to control cell fates. These channels and pores modulate concentrations of intracellular cations $Ca^{2+}$ and $H^+$, intracellular anions ADP, ATP, malate, and glutamate, and intracellular thiols, glutathione, cysteine, thioredoxin, and biopterin. By these means, these channels can indirectly modulate redox-sensitive sites in signal transduction, proliferation, development, transcription, apoptosis pathways, and necrosis pathways, thereby dictating cell fates.

Many agents that can directly modulate these pores are in use for anti-proliferative therapies, notably as treatments for hyperproliferative syndromes and cancer (see Miccoli et al., *J Nat. Cancer Inst.* 90: 1401–1406, 1998; Ravagnan et al., *Oncogene* 18: 2537–2546, 1999; Larochette et al., *Exp. Cell Res.* 249: 413–471, 1999). Three broad classes of modulators are in use—lipophilic peptides, lipophilic amines, and thiol redox-reactive cyclic amines.

Lipophilic peptides are useful as antiproliferative and anti-inflammatory therapies. These peptides, primarily Bax, Bcl-2, and cyclosporine A, either block or bypass mitochondrial transmembrane channels by creating pores of oxidized polymerized peptides of variable permeability in the mitochondrial outer membranes (see De Giorgi et al., *FASEB J* 10: 607–609, 2002). The redox-insensitive lipophilic benzo amines are useful in cancer therapy. Diazepam and lonidamine, for example, bind to mitochondrial benzodiazepine receptors in the mitochondrial matrix, block mitochondrial electron flow and ATP synthesis, and induce apoptotic and necrotic death in rapidly growing cells (see Miccoli et al., *J Nat. Cancer Inst.* 90: 1401–1406, 1998). As for the thiol redox-sensitive cyclic amines, their usefulness in mitochondrial transmembrane pore modulation has not been fully explored.

Diamide (diazenedicarboxylic acid), the thiol cross-linking non-cyclic amine, completely opens mitochondrial transmembrane pores, which causes the mitochondrial transmembrane potential to collapse, with dissipation of H+(pH) gradients, production of $O_2^-$, and release of the apoptosis inducing factors cytochrome c and AIF. Consequently, cells slowly die depending on their supplies of reduced thiols, primarily glutathione (see Zamzami et al., *Oncogene* 16: 1055–1062, 1998). However, although a potent eradicator of cancer cells and other proliferating cells of the host, this cross-linking non-cyclic amine is too toxic for clinical uses.

Other cyclic lipophilic amines, such as amino phthalazine diones, biopterins, and rhodamines, which accumulate electrostatically in mitochondrial transmembrane pores and accept and release both electrons and protons, reversibly serve as both electron and pH buffers in the polarized channels and pores. In this manner, both the ionic and oxidative status of the labile sulfhydryl in ANT are maintained by these redox- and pH-sensitive amines. The cyclic amines thus affect voltage in the channels, and fluxing electrons are either trapped by $O_2$ as $O_2^-$ or proceed downstream with production of $H_2O$ and ATP. At low doses of these compounds, electron flow increases, electrons proceed downstream to $H_2O$, ATP production increases, DNA synthesis and cell proliferation increase, and cell death is aborted. At high doses, electron flow to $H_2O$ decreases, substrate anion translocations falter, membrane potential declines, ATP production ceases, as does electron flow, and cells go into a quiescent $G_0/G1$ phase or apoptosis.

With the lipophilic tetramethyl-rhodamine, many electrons are shunted directly to $O_2$, with the result that $O_2^-$ accumulates, mitochondrial transmembrane pores open with loss of membrane potential, and apoptotic and necrotic pathways are activated (see De Giorgi et al., *FASEB J.* 10: 607–609, 2002). Phthalazine diones such as 5-amino phthalazine dione, with reduced biopterins, thiols, or lipoic acid, modulate electron flow to $O_2^-$ or $H_2O$ (Lynn et al., unpublished). Specifically, at low doses, amino phthalazine diones upregulate the host's immune responses to eradicate cancerous cells. At high doses, amino phthalazine diones stop proliferation of hyperproliferating cancerous cells. Thus, by upregulating or downregulating particular cells, amino phthalazine diones are useful in cancer treatment (see Tzyb et al., *Int. J. Immunorehabilitation* 12: 398–403, 1999).

Modulation of mitochondria by these bifunctional cyclic phthalazines is most effective in controlling cell fate in proliferating cells that are deficient in biological thiol redox buffers (see Armstrong and Jones, *FASEB J.* 16: (online), Jun. 7, 2002; Larochette et al., *Exp. Cell Res.* 249: 413–471, 1999), or in proliferating cells deficient in cell cycle checkpoint genes (Yan et al., *Genes and Dev.*, in press). Thus, redox- and pH-sensitive amines that buffer by dually modulating mitochondrial transmembrane pores and anion channels are clinically useful both in preventing and treating hyperproliferation states such as cancers.

EXAMPLE 15

Use of Phthalazine Diones in Chronic Dys-metabolic Syndromes

Food intake, especially fat, with excess deposition of fat in adipose cells, causes production and secretion of large amounts of the adipose tissue defense peptide hormones—resistin, leptin, tumor necrosis factor, adiponectin. These collagen- and complement-like peptides facilitate uptake of glucose and combustion of long-chain fatty acids via peroxisome proliferator receptors (PPAR) and mitochondria, with production of heat in the muscle mitochondria, facilitated by activating uncoupling proteins in mitochondria. This removal of the excess fatty acids relieves the fatty acid-induced stress in adipocytes and also lowers levels of toxic, free fatty acids in blood.

However, in time, with prolonged intake of fatty foods, as in affluent societies, and with consequent excessive storage of fat in adipose cells, these overstuffed fat cells produce and secrete more of the inflammatory cytokines, tumor necrosis factor, and resistin (a redox-sensitive adipokine), at the expense of secretion of adiponectin. In aging Americans with overstuffed fat cells, blood levels of tumor necrosis factor and resistin are high; adiponectin and plasminogen-activator inhibitors are low; glucose, free fatty acids, triglyceride, and insulin are high; and the PPARγ/RXR (retinoid X receptor) complexes in fat and muscle cells are underactivated. Vascular accidents in heart and brain, with atherosclerotic plaques, are also greatly increased in these insulin-resistant individuals. This syndrome, now epidemic, is called Syndrome X.

Syndrome X is currently and partially treated with various benzolated thiazolidinediones. These cyclic nitrogenous diketones, which are structurally similar to the phthalazine diones of the present invention, bind to the promoters of PPARγ in the nucleus and activate multiple gene families that activate peroxisomal fatty acid oxidation with increased production of adiponectin and catalase, increased glucose uptake, and increased production of enzymes required for fatty acid synthesis and oxidation and for terminal differentiation in adipocytic precursor cells. At high concentrations, these diketone ligands of PPARγ also block proliferation and activities of activated macrophages, endothelial cells, microglia in brain, and probably proliferating smooth muscle cells in atheromatous plaques. Thus, benzolated thiazolidinediones are useful in preventing Syndrome X and its downstream sequelae, including insulin resistance, vascular degeneration with hypertension, macrophage proliferation and hyperactivity, with plaque formation and Type II Diabetes.

Benzolated phthalazine diones chemically resemble benzolated thiazolidinediones and are known to reproduce some functions of benzolated thiazolidinediones, perhaps as a ligand for PPARγ. In particular, amino phthalazine diones, like benzolated thiazolidinediones, also stop proliferation and suppress destructive overactivity by inflammatory and adipose cells, with production of many inflammogens. Whether amino phthalazine diones are actually a ligand for PPARγ, can suppress tumor necrosis factor and resistin secretion in adipocytes and macrophages, and increase secretion of adiponectin by adipocytes are under investigation. Whether benzolated thiazolidinediones, like amino phthalazine diones, can bind to benzodiazepine receptors in mitochondria and alter activity of ion channels and megapores in mitochondria are also not presently known.

Since benzolated thiazolidinediones are very poor redox agents, it is not likely that they directly modulate thiol redox status in mitochondrial voltage-dependent channels or in the permeability pores. In contrast, since amino phthalazine diones probably possess these dual defensive functions, as a redox buffer in mitochondria and as a PPAR activator in the nucleus, amino phthalazine diones promise a better and more complete therapy for all symptoms of Syndrome X. Combinational therapy with benzolated thiazolidinediones and amino phthalazine diones, plus thiols and other redox adjuvants, may be the treatment of choice for prevention of downstream sequelae of Syndrome X, such as hyperglycemia, hyper fatty acidemia, increased tumor necrosis factor and resistin levels, hypo-adiponectin-emia, hyper or hypo insulin-emia, impaired thiol redox status (hypo-glutathione and cysteine-emia), PPARγ inactivity, and mitochondrial energy uncoupling with elevated $H_2O_2$, OHOO., and cytoplamic cytochrome c.

Repeated monitoring of the above adipose hormones during treatments with benzolated thiazolidinediones/amino phthalazine dione/thiol therapies will be required to establish specific dosage and efficacy for each individual. Since with each individual, downstream sequelae of Syndrome X, including insulin resistance with long-chain fatty acid poisoning, vary greatly, dose adjustments according to individual responses, as measured by the above adipokine markers, will be required for optimum therapy.

EXAMPLE 16

Stress-Induced Phosphorylation Signaling and Phthalazine Diones

The major survival and growth signaling pathways in some cells involve the phosphorylation of epidermal growth factor receptor (EGFR), mitogen-activated protein kinases (MAPK), extracellular signal-regulated kinases (ERK), phosphoinositol-3 kinase, protein kinase B, and inhibitor KB kinase (IKK), the kinase controlling $NF_KB$ activity, $NF_KB$ being a major stress-induced transcription factor. The cell death pathway is controlled by c-Jun N-terminal kinase (JNK), p38, and p53, another stress-induced transcription factor.

Oxidants such as $H_2O_2$ activate intracellular phosphorylation cascades responsible for cell survival and growth and for cell death via apoptosis and necrosis (see Wang et al., *J. Biol. Chem.* 275: 14624–14631, 2000). Low doses of $H_2O_2$ directly and rapidly activate the survival pathway, using primarily Akt, PI-3K, EGFR, and $NF_KB$. The apoptotic factors Bad and caspase 9 are also downregulated by low doses of $H_2O_2$. Higher doses of $H_2O_2$ or prolonged exposure to $H_2O_2$ activate the cell death pathways involving JNK, p53, Bax, sphingomyelinase, caspases, and the apoptosis signaling kinase AsK-1.

Thus, oxidants, much like the phthalazine diones of the invention, activate either cell survival or cell death pathways, depending on dosage. However, $H_2O_2$ is not a buffer and cannot maintain optimal redox potentials sufficient to maintain cell signaling and growth. $H_2O_2$ also does not scavenge the excess reactive oxygen species produced by activated cell growth pathways. The ability of phthalazine diones, especially amino phthalazine diones, to provide both oxidizing and reducing potential to mitochondria, peroxisomes, and cytoplasmic signaling pathways makes these compounds an ideal in vivo redox buffer capable of dictating most cell fates.

In disease states where signal-induced cell death rates exceed cell growth rates—as in various neurodegenerative syndromes such as Alzheimer's, ataxia telangiectasia, Parkinson's, Multiple System Atrophy, or AIDS—or in disease states where autonomous growth signaling rates exceed cell death rates—as in cancers, ataxia telangiectasia, trichothiodystrophy, or hyperinflammatory syndromes—amino phthalazine diones dictate cell fates by buffering the aberrant cellular redox potentials up or down, both in the stressed host and in any invading or overactivated cell. The phthalazine diones of the invention are likely to be therapeutically useful for modulating aberrant phosphorylation signaling syndromes involved in cell growth and death.

EXAMPLE 17

Neuronal Overactivity and Amino Phthalazine Diones

In Parkinson's disease, neurons of the subthalamic nucleus (STN) become imbalanced and discharge too much. This 4 Hz oscillatory overactivity in STN neurons of patients with the classical symptoms of parkinsonism—bradykinesia, rigidity, and tremor—is a major etiologic factor in Parkinson's. Suppression of this oscillatory activity by intra-STN injection of various agents such as lidocaine and muscimol (a gamma aminobutyric acid-A receptor agonist) or chronic electrical (2V) stimulation promptly relieves these parkinsonian symptoms.

The cause of this 4 Hz overactivity in only a few STN neurons is not known (see Levy et al., *Brain* 124: 2105–2118, 2001; Luo et al., *Science* 298: 425–429, 2002; Limousin et al., *New England J of Med.* 339: 1105–1111, 1998; Alvarez et al., *Movement Disorders* 16: 72–78, 2001). The downstream effects of STN overactivity in substantia nigra reticulata, globus pallidus, and motor thalamus are likely to be responsible for multiple movement disorders.

Since maintaining this excessive and imbalanced 4 Hz oscillation requires increased energy expenditures, agents such as 5-amino phthalazine dione, which can modulate thiol redox status, downregulate mitochondrial energy production, and gain access to the overactivated STN neurons, can potentially suppress the 4 Hz overactivity and thereby suppress and modulate the downstream network activities responsible for the symptoms. Daily intraperitoneal injections of 200 $\mu$g of 4-sodium amino phthalazine dione significantly delays the progress of the movement disorder with paralysis induced by MOMU-LV-Ts1 virus in mice. Whether this is due to suppression of oscillatory activity in neurons, suppression of virus-induced astrocytic inflammatory responses, or both is under investigation. Amino phthalazine diones should, however, suppress both the neuronal and astrocytic overactivity.

The foregoing material describes various aspects of the invention and how the invention may be practiced. The description of the invention is not intended to be exhaustive of the many different embodiments of the invention. Although the foregoing invention has been described in some detail by way of illustration and example, to aid understanding, it will be readily apparent to those of ordinary skill in the art, in light of the teachings of this invention, that certain changes and modifications may be made to the invention without departing from the spirit or scope of the appended claims.

What is claimed is:

1. A method of modulating metabolic distress in cells, comprising administering a therapeutically effective amount of a phthalazine dione or its pharmaceutically acceptable analog to cells in treating a condition selected from the group consisting of insulin resistance, hyperglycemia, hyper fatty acidemia, hyperinsulinemia, hypoadiponectinemia, Syndrome X, a condition associated with a regulatory gene defect, tumors associated with the p53 transcription factor, brain, or thymus, xeroderma pigmentosum, ataxia telangiectasia, trichothiodystrophy, Down's syndrome, burns, psoriasis, rheumatoid arthritis, leprosy and a neurological disorder, wherein said neurological disorder is selected from the group consisting of Parkinson's disease, Huntington's disease, Bloom's disease, amyotrophic lateral sclerosis, Cockayne syndrome and dementia.

2. The method of claim 1, wherein the phthalazine dione is administered together with an additive selected from the group consisting of adjuvant, carrier, excipient, and stabilizer.

3. The method of claim 2, wherein the phthalazine dione comprises a pharmaceutically acceptable form selected from the group consisting of tablet, capsule, granule, powder, solution, suspension, microsphere, liposome, colloid, lyophilized composition, gel, lotion, ointment, cream, spray, and suppository.

4. The method of claim 3, wherein the phthalazine dione is administered by a means selected from the group consisting of intravenous, intramuscular, intraperitoneal, subcutaneous, oral, nasal, mucosal, transdermal, parenteral, vaginal, and rectal.

5. The method of claim 4, wherein the method is used in combination with a standard therapy selected from the group consisting of radiation, chemotherapy, surgery, drug therapy, and nutrition.

6. The method of claim 1, wherein the phthalazine dione is an amino derivative.

* * * * *